United States Patent
Xu et al.

(10) Patent No.: US 12,264,145 B2
(45) Date of Patent: Apr. 1, 2025

(54) CRYSTAL FORM F OF TRELAGLIPTIN AND PREPARATION METHOD THEREOF

(71) Applicant: GUANGDONG UNIVERSITY OF TECHNOLOGY, Guangzhou (CN)

(72) Inventors: Kailin Xu, Guangzhou (CN); Jierui Huo, Guangzhou (CN); Jianping Wang, Guangzhou (CN); Shungquan Mu, Guangzhou (CN); Suqing Zhao, Guangzhou (CN)

(73) Assignee: GUANGDONG UNIVERSITY OF TECHNOLOGY, Guangzhou (CN)

( * ) Notice: Subject to any disclaimer, the term of this patent is extended or adjusted under 35 U.S.C. 154(b) by 21 days.

(21) Appl. No.: 18/522,287

(22) Filed: Nov. 29, 2023

(65) Prior Publication Data

US 2024/0199574 A1    Jun. 20, 2024

(51) Int. Cl.
C07D 401/04    (2006.01)

(52) U.S. Cl.
CPC ........ C07D 401/04 (2013.01); *C07B 2200/13* (2013.01)

(58) Field of Classification Search
CPC .................... C07D 401/04; C07B 2200/13
See application file for complete search history.

(56) References Cited

U.S. PATENT DOCUMENTS

| | | | |
|---|---|---|---|
| 10,292,983 B2 | 5/2019 | Mcwherter | |
| 10,487,090 B2 | 11/2019 | Calimsiz et al. | |
| 10,934,279 B2 | 3/2021 | Aspnes et al. | |

FOREIGN PATENT DOCUMENTS

| | | | | |
|---|---|---|---|---|
| CN | 104003975 A | 8/2014 | | |
| CN | 104603123 A | 5/2015 | | |
| CN | 105524041 A | 4/2016 | | |
| CN | 105693691 A | * 6/2016 | | |
| CN | 111440145 A | * 7/2020 | | |
| WO | WO-2008067465 A1 | * 6/2008 | ........... | C07D 401/04 |

OTHER PUBLICATIONS

CN-105693691-A—Google Patents—English Machine Translation (Year: 2016).*
CN-111440145-A—Google Patents—English Machine Translation (Year: 2020).*

* cited by examiner

*Primary Examiner* — Clinton A Brooks
*Assistant Examiner* — Josmalen M. Ramos-Lewis
(74) *Attorney, Agent, or Firm* — True Shepherd LLC; Andrew C. Cheng

(57) ABSTRACT

A method for preparing a novel crystal form F of trelagliptin includes: adding a mediating protein into the trelagliptin to obtain a mixture, and introducing a mechanochemical action on the mixture for transformation of a crystal form of the trelagliptin to obtain the novel crystal form F of trelagliptin. The preparation method does not require any organic solvent and thus will not lead to an organic solvent residue to affect the safety of medication. In addition, the preparation method is less time-consuming than a solvent crystallization method, is easy to allow green industrial production, and has characteristics such as simplicity, high efficiency, safety, and environmental friendliness.

2 Claims, 3 Drawing Sheets

CRYSTAL FORM F OF TRELAGLIPTIN AND PREPARATION METHOD THEREOF

CROSS-REFERENCE TO RELATED APPLICATIONS

This application claims priority to Chinese Patent Application No. 202211577018.9 with a filing date of Dec. 8, 2022. The content of the aforementioned application, including any intervening amendments thereto, is incorporated herein by reference.

TECHNICAL FIELD

The present disclosure belongs to the technical field of drug preparation, and in particular relates to a novel crystal form of trelagliptin, and a method for protein-mediated preparation of the novel crystal form of trelagliptin under a mechanochemical action.

BACKGROUND

It is reported by the Diabetes Atlas 10th edition of the International Diabetes Federation (IDF) in 2021 that about 537 million people worldwide suffer from diabetes, and in 2045, a number of diabetes patients will reach about 783 million and diabetes will become one of the leading causes for human death worldwide. In addition, there is a high prevalence rate of diabetes in adults, and a treatment rate, an awareness rate, and a control rate of diabetes continue to be low. A number of type II diabetes cases is about 90% of a total number of diagnosed diabetes cases. Type II diabetes is mainly caused by insufficient insulin secretion and an inadequate response of a body to insulin. In type II diabetes, insulin secretion increases initially, but pancreatic β cells undergo functional defects over time, resulting in a decrease in insulin secretion. Currently, oral hypoglycemic agents (OHAs) are still one of the major manners for treating type II diabetes, and the development of drugs for treating type II diabetes that have excellent hypoglycemic effects and small side effects is a major breakthrough for solving this major human health problem.

Trelagliptin is a long-acting dipeptidyl peptidase-4 (DPP-4) inhibitor developed by Takeda in Japan. The DPP-4 inhibitor can competitively bind to an active site of DPP-4 to reduce a catalytic activity of DPP-4 and inhibit the degradation of glucagon-like peptide-1 (GLP-1), thereby increasing a concentration of GLP-1 in blood to play a hypoglycemic role. It has been reported in the literature that trelagliptin exhibits a more potent DPP-4-inhibiting effect than other DPP-4 inhibitors, where a DPP-4-inhibiting effect of trelagliptin is 4 times a DPP-4-inhibiting effect of alogliptin and 12 times a DPP-4-inhibiting effect of sitagliptin. The DPP-4-inhibiting effect of trelagliptin has characteristics such as reversibility, substrate competition, and slow binding, and thus is long-lasting. Trelagliptin only needs to be taken orally once a week, and has excellent patient compliance. Therefore, trelagliptin is a desired drug for treating type II diabetes.

However, trelagliptin is a water-insoluble compound, and is generally used in a solid (crystalline) form in clinical formulations. According to statistics, 50% or more of chemical drugs have a polymorphism problem. Different crystal forms of a drug have different physical and chemical properties, which can significantly affect the quality, bioavailability, efficacy, and safety of the drug. Thus, the research on crystal forms of a drug is a non-negligible important content in the research and development of the drug. The discovery and regulation of crystal forms of a drug is a key to the research on the crystal forms of the drug, and is a basis for screening an advantageous crystal form with excellent physical and chemical properties, remarkable efficacy, and high safety. Therefore, it is of great significance to investigate a crystal form of trelagliptin and a preparation method of the crystal form.

At present, there are many patents and references for research on a crystal form of trelagliptin and a preparation method of the crystal form, such as a world patent WO2014127735-A1 and Chinese patents CN105384724, CN105693691, and CN104003975. However, in the prior art, one or more organic solvents are used in a preparation method of a trelagliptin crystal. The world patent WO2014127735-A1 (title of the invention: Crystal form A of trelagliptin useful for e.g. preparing medicine for treating disease mediated by dipeptidyl peptidase IV, exhibits powder X-ray diffraction pattern, and has diffraction peak at specified angle) discloses a trelagliptin crystal A. 2θ values in an X-ray powder diffraction (XRPD) pattern of the trelagliptin crystal A are 5.7±0.2°, 11.4±0.2°, 12.5±0.2°, 16.8±0.2°, 17.1±0.2°, 19.4±0.2°, 19.9±0.2°, 20.5=0.2°, 22.5±0.2°, 22.9±0.2°, and 29.1±0.2°. Organic solvents are used in large quantities in a preparation method of the trelagliptin crystal A. The Chinese patent CN105384724 (title of the invention: crystal forms of fluorinated compounds and preparation methods thereof) discloses crystal forms II and IV of trelagliptin and preparation methods thereof. 2θ values in an XRPD pattern of the crystal form II are 20.04°, 20.85°, and 21.86°, and 2θ values in an XRPD pattern of the crystal form IV are 16.28°, 20.03°, 22.30°, and 27.55°. In a preparation method of the crystal form II, organic solvents such as butanone, n-pentane, cyclohexane, and n-heptane are used. The crystal form IV is obtained by heating the crystal form II at a high temperature. The Chinese patent CN105693691 (title of the invention: novel crystal form of high-purity trelagliptin and preparation thereof) discloses a method for preparing a novel crystal form of high-purity trelagliptin. In this method, raw materials are first placed in a mixed solution of an organic solvent and alkali liquor and heated to allow a reaction under reflux to obtain a crude trelagliptin product, and then the crude trelagliptin product is subjected to recrystallization in an organic solvent for removing isomers to obtain the novel crystal form of high-purity trelagliptin. 2θ values in an XRPD pattern of the novel crystal form of trelagliptin are 4.8±0.2°, 9.6±0.2°, 18.4±0.2°, and 18.9±0.2°. The Chinese patent CN104003975 (title of the invention: novel solid forms of trelagliptin, and preparation methods and uses thereof) discloses six crystal forms of trelagliptin and preparation methods thereof. The six crystal forms include a crystal form A, a crystal form B, a crystal form C, a crystal form D, a crystal form E, and an amorphous form. In the preparation methods of these crystal forms of trelagliptin other than the amorphous form, toxic organic solvents are used in large quantities, including tetrahydrofuran (THF), acetone, acetonitrile, or the like.

In most of the existing drug preparation techniques, an organic solvent is used as a medium, which can effectively improve a yield of a product, but inevitably causes problems such as potential safety hazards of medication and environmental pollution. In the above preparation methods, toxic organic solvents such as THF, acetonitrile, acetone, and halogenated hydrocarbons are often used, and reaction processes mostly have strict temperature requirements. The purification of trelagliptin through recrystallization is time-consuming and may lead to problems such as an organic solvent residue in a final product, which not only affects the safety of active pharmaceutical ingredients (APIs), but also has serious adverse effects on the environment and the health of drug producers.

SUMMARY OF PRESENT INVENTION

In view of the shortcomings in the prior art, the present disclosure provides a method for solvent-free preparation of a novel crystal of trelagliptin. This method is eco-friendly and fast and has a high yield. In this method, trelagliptin is induced by a protein under a sufficient mechanical action to produce a novel crystal form F, where the protein is used instead of a toxic organic solvent in the conventional preparation method. In addition, mechanical ball-milling is adopted in this method to ensure the quality uniformity of a final product and a yield.

Specific technical solutions of the present disclosure are as follows:

The present disclosure provides crystalline trelagliptin with a structural formula as follows:

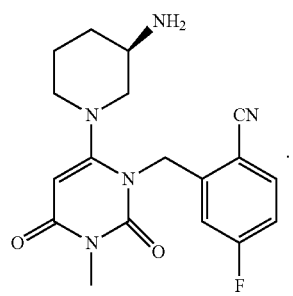 [SMILES: Cn1c(=O)cc(N2CCC[C@@H](N)C2)n(Cc2cc(F)ccc2C#N)c1=O]

The crystalline trelagliptin of the present disclosure refers to a novel crystal form F of trelagliptin, which is obtained through protein-mediated transformation of a crystal form of trelagliptin under a mechanochemical action. This preparation method avoids the hazards of organic reagents and the influence of an organic solvent residue in API on the safety of medication, can ensure the safety of the drug during preparation and use, and is eco-friendly.

Preferably, an XRPD pattern of the crystalline trelagliptin has corresponding diffraction peaks at 2θ values of 11.47°, 12.41°, 13.21°, 14.46°, 16.13°, 16.93°, 17.40°, 18.49°, 19.24°, 19.80°, 20.37°, 21.76°, 22.76°, 23.21°, 23.75°, 25.08°, 25.52°, 26.02°, 28.02°, 29.54°, 30.92°, 34.12°, and 34.98°, or has characteristics represented by the XRPD pattern shown in FIG. 1.

The present disclosure also provides a preparation method of the crystalline trelagliptin, including the following steps:

adding trelagliptin and a protein in a specified mass ratio to an agate ball-milling tank, adding agate mill balls of a corresponding size in a specified proportion, and conducting mechanical ball-milling under set ball-milling parameters to obtain the crystalline trelagliptin.

In the present disclosure, a common protein is used to induce the transformation of a crystal form of trelagliptin. Numerous diversified complicated binding sites of the protein can interact with a drug molecule to change a molecular conformation. Thus, the small amount of the protein added can interact with the drug molecule during the ball-milling to induce a conformational change of the drug molecule and drive the re-assembly of the drug molecule. The preparation method is simple, eco-friendly, cost-effective, and easy to implement, has a high product yield, and involves simple production devices. The whole production process of the preparation method is easy to control and thus is suitable for large-scale production. In addition, the preparation method has high economic benefits, and does not require any organic solvent, which is eco-friendly, energy-saving, and highly-safe.

A mass ratio of the trelagliptin to the protein is preferably (2-120):1 and more preferably (10-100):1.

The crystal form transformation is conducted at a temperature of preferably 10° C. to 40° C. and more preferably 15° C. to 35° C.

The crystal form transformation of trelagliptin under the mechanochemical action is conducted for preferably 0.5 h to 6 h and more preferably 1 h to 3 h.

In the present disclosure, the novel crystal form F of trelagliptin can be prepared under a mechanical action such as manual milling and ball-milling, and the ball-milling is preferably adopted to provide a mechanical force.

Preferably, the mechanical ball-milling is conducted at a rotational speed of 400 r/min to 650 r/min.

The protein in the present disclosure includes, but is not limited to, bovine serum albumin (BSA), human serum albumin (HSA), ovalbumin, and pepsase.

Compared with the existing references and patent reports, the present disclosure has the following advantages:

1. The trelagliptin crystal prepared in the present disclosure is a novel crystal form F, and has uniform particles.

2. The mechanical ball-milling-based preparation method of the present disclosure is relatively simple and controllable, can minimize an error caused by operations of different batches, and can ensure a uniform quality of final products of different batches and a relatively-high yield. Therefore, the preparation method is suitable for industrial production.

3. The present disclosure provides a novel crystal form F of crystalline trelagliptin and a preparation method thereof to solve the problem that the existing methods for preparing a trelagliptin crystal all require one or more toxic organic solvents, which affects the safety of APIs and has serious adverse effects on the environment and the health of drug producers. The preparation method provided in the technical solution of the present disclosure does not require any organic solvent. As a result, the preparation method of the present disclosure will not cause pollution to both the drug itself and the environment, is eco-friendly, and will not adversely affect the health of a drug producer.

4. Only a small amount of a protein is used as a crystal form-transformation inducer in the preparation method provided in the technical solution of the present disclosure, which can ensure the safety of the drug during both preparation and use.

5. Materials used in the preparation method provided in the technical solution of the present disclosure are cheap and easily-available and have relatively-low storage requirements, resulting in a low production cost and a high economic benefit.

In summary, the present disclosure provides crystalline trelagliptin, which is a novel crystal form F of trelagliptin. The present disclosure provides a method for protein-mediated preparation of a novel crystal form F of trelagliptin under a mechanochemical action, which avoids the hazards of organic reagents and the influence of an organic solvent residue in API on the safety of medication, can ensure the safety of the drug during preparation and use, and is eco-friendly.

BRIEF DESCRIPTION OF THE DRAWINGS

In order to clearly illustrate the technical solutions in the embodiments of the present disclosure or in the prior art, the accompanying drawings required for the description of the embodiments or the prior art are briefly described below.

DETAILED DESCRIPTION OF THE EMBODIMENTS

The technical solutions in the embodiments of the present disclosure will be clearly and completely described below. Apparently, the described embodiments are merely some rather than all of the embodiments of the present disclosure. All other embodiments obtained by those of ordinary skill in the art based on the embodiments of the present disclosure without creative efforts shall fall within the protection scope of the present disclosure.

The trelagliptin used in the embodiments of the present disclosure was purchased from Shanghai Yingrui Biopharma Co., Ltd., which is not limited here.

Example 1

Figure 1:
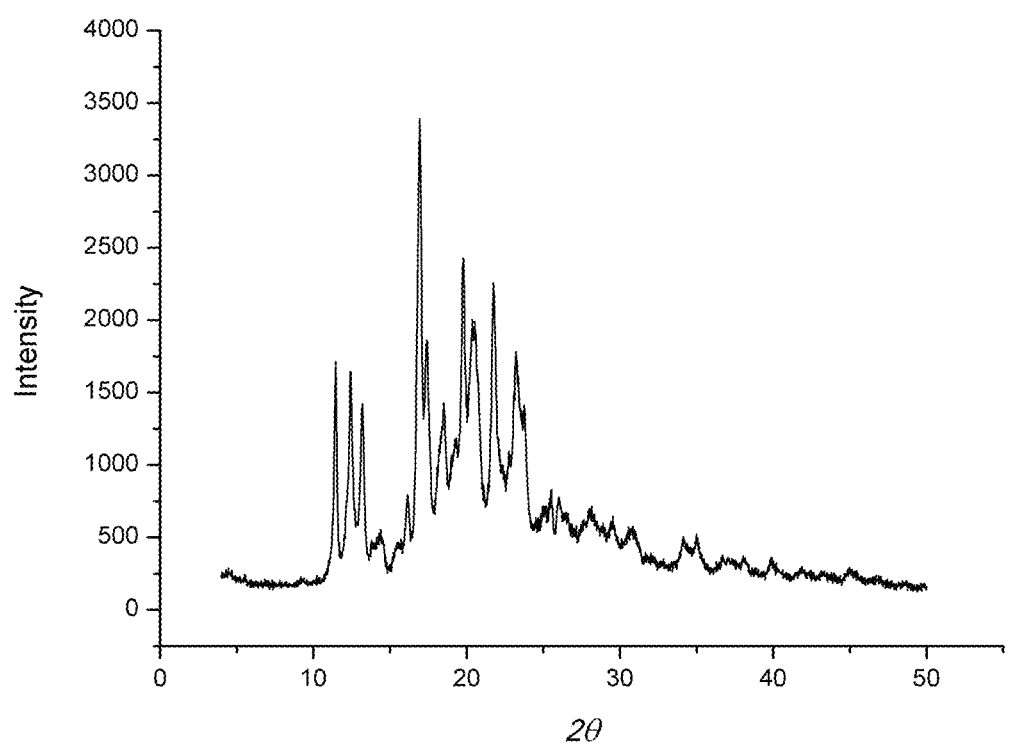
FIG. 1 is an XRPD pattern of the crystalline trelagliptin provided in Example 1 of the present disclosure.

20 g of trelagliptin and 0.2 g of BSA were accurately weighed and added to a 500 mL ball-milling tank (a mass ratio of the trelagliptin to the protein was 100:1), mill balls were added, the ball-milling tank was placed in a 25° C. ball mill, and ball-milling was conducted at a rotational speed of 650 r/min for 1 h to obtain a white trelagliptin powder. The white trelagliptin powder obtained in this example was subjected to XRPD analysis, and an XRPD pattern of the crystalline trelagliptin was recorded under the following conditions: room temperature: 25° C., and relative humidity: lower than 60%; and X'Pert PRO polycrystalline X-ray diffractometer (PANalytical, Netherlands), Cu Kα radiation ($\lambda$=1.5406 Å), tube voltage: 40 kV, tube current: 40 mA, 2θ scanning range: 4° to 50°, step size: 0.01313°, and counting time: 30 ms/step. FIG. 1 is an XRPD pattern of the new crystal form F of trelagliptin obtained in Example 1 of the present disclosure, and it can be seen that the XRPD pattern of the novel crystal form F of trelagliptin has corresponding diffraction peaks at 2θ values of 11.47°, 12.41°, 13.21°, 14.46°, 16.13°, 16.93°, 17.40°, 18.49°, 19.24°, 19.80°, 20.37°, 21.76°, 22.76°, 23.21°, 23.75°, 25.08°, 25.52°, 26.02°, 28.02°, 29.54°, 30.92°, 34.12°, and 34.98°.

Figure 2:
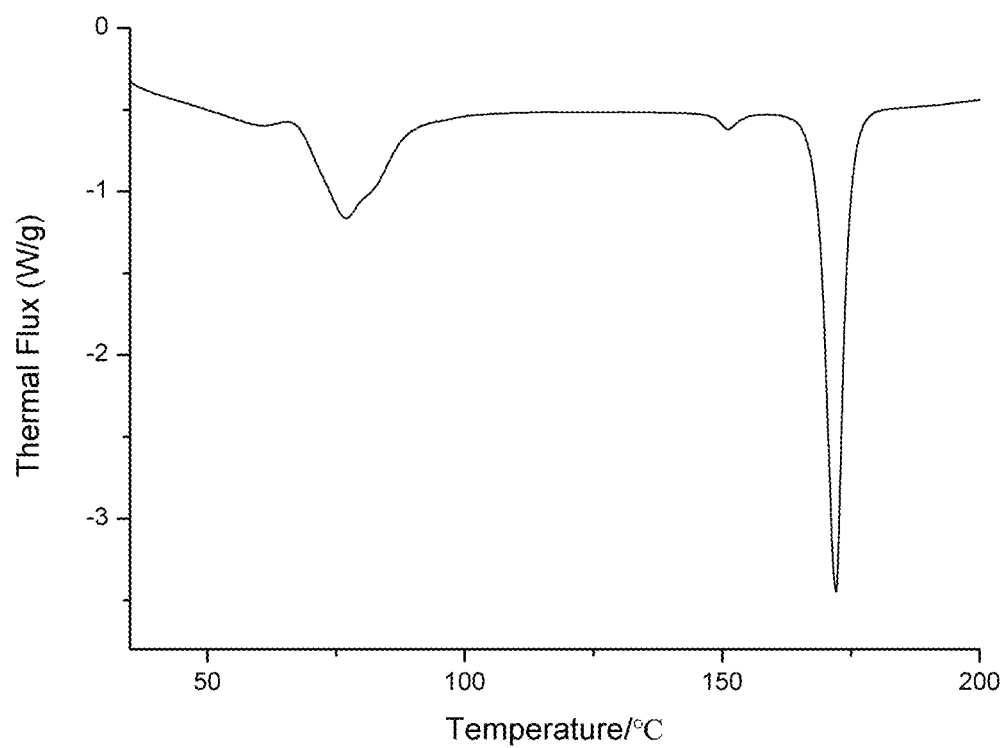
FIG. 2 is a differential scanning calorimetry (DSC) curve of the crystalline trelagliptin provided in Example 1 of the present disclosure.

The white trelagliptin powder obtained in this example of the present disclosure was subjected to DSC analysis, and a DSC curve of the novel crystal form of trelagliptin was recorded under the following conditions: Q200 differential scanning calorimeter (TA of the United States), $N_2$ protection, air flow rate: 20 mL/min, detection temperature range: 30° C. to 200° C., and heating rate: 10° C./min. FIG. 2 is a DSC curve of the novel crystal form F of trelagliptin in Example 1 of the present disclosure, and it can be seen that the novel crystal form F of trelagliptin has an endothermic peak at 150° ° C. to 180° C. or has characteristics represented by the DSC curve shown in FIG. 2.

Figure 3:
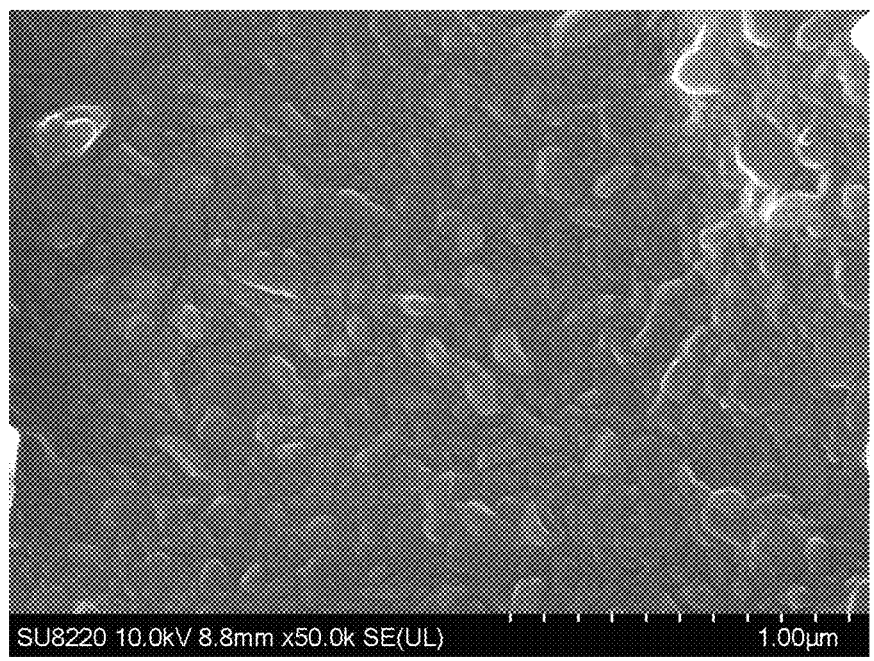
FIG. 3 is a scanning electron microscopy (SEM) image of the crystalline trelagliptin provided in Example 1 of the present disclosure.

The novel trelagliptin crystal obtained in this example was subjected to SEM analysis, and an SEM image of the novel trelagliptin crystal was acquired as follows: a small amount of dry sample particles were taken and evenly spread on a small metal round table to which a small piece of a double-sided tape was attached, and then a thin layer of platinum was sprayed under nitrogen protection to make the sample electrically-conductive to obtain a test sample; and the test sample was subjected to SEM analysis under the following conditions: Hitachi SU8220 field emission scanning electron microscope, and detection voltage: 10.0 kV. An SEM analysis result is shown in FIG. 3, and it can be seen that the prepared novel crystal form F of trelagliptin is granular.

Example 2

10 g of trelagliptin and 0.2 g of BSA were accurately weighed and added to a 500 mL ball-milling tank (a mass ratio of the trelagliptin to the protein was 50:1), mill balls were added, the ball-milling tank was placed in a 25° C. ball mill, and ball-milling was conducted at a rotational speed of 650 r/min for 0.5 h to obtain a novel crystal form F of trelagliptin.

Example 3

15 g of trelagliptin and 0.5 g of BSA were accurately weighed and added to a 500 mL ball-milling tank (a mass ratio of the trelagliptin to the protein was 30:1), mill balls were added, the ball-milling tank was placed in a 35° C. ball mill, and ball-milling was conducted at a rotational speed of 650 r/min for 1 h to obtain a novel crystal form F of trelagliptin.

Example 4

15 g of trelagliptin and 0.5 g of BSA were accurately weighed and added to a 500 mL ball-milling tank (a mass ratio of the trelagliptin to the protein was 30:1), mill balls were added, the ball-milling tank was placed in a 25° C. ball mill, and ball-milling was conducted at a rotational speed of 400 r/min for 1.5 h to obtain a novel crystal form F of trelagliptin.

Example 5

20 g of trelagliptin and 1 g of BSA were accurately weighed and added to a 500 mL ball-milling tank (a mass ratio of the trelagliptin to the protein was 20:1), mill balls were added, the ball-milling tank was placed in a 15° C. ball mill, and ball-milling was conducted at a rotational speed of 650 r/min for 1 h to obtain a novel crystal form F of trelagliptin.

Example 6

10 g of trelagliptin and 1 g of BSA were accurately weighed and added to a 500 mL ball-milling tank (a mass ratio of the trelagliptin to the protein was 10:1), mill balls were added, the ball-milling tank was placed in a 25° C. ball mill, and ball-milling was conducted at a rotational speed of 500 r/min for 0.5 h to obtain a novel crystal form F of trelagliptin.

Example 7

20 g of trelagliptin and 0.2 g of pepsase were accurately weighed and added to a 500 mL ball-milling tank (a mass ratio of the trelagliptin to the protein was 100:1), mill balls were added, the ball-milling tank was placed in a 25° C. ball mill, and ball-milling was conducted at a rotational speed of 650 r/min for 2 h to obtain a novel crystal form F of trelagliptin.

Example 8

15 g of trelagliptin and 0.5 g of pepsase were accurately weighed and added to a 500 mL ball-milling tank (a mass ratio of the trelagliptin to the protein was 30:1), mill balls were added, the ball-milling tank was placed in a 35° C. ball mill, and ball-milling was conducted at a rotational speed of 650 r/min for 1 h to obtain a novel crystal form F of trelagliptin.

Example 9

15 g of trelagliptin and 0.5 g of pepsase were accurately weighed and added to a 500 mL ball-milling tank (a mass ratio of the trelagliptin to the protein was 30:1), mill balls were added, the ball-milling tank was placed in a 25° C. ball mill, and ball-milling was conducted at a rotational speed of 400 r/min for 3 h to obtain a novel crystal form F of trelagliptin.

Example 10

20 g of trelagliptin and 1 g of pepsase were accurately weighed and added to a 500 mL ball-milling tank (a mass ratio of the trelagliptin to the protein was 20:1), mill balls were added, the ball-milling tank was placed in a 15° C. ball mill, and ball-milling was conducted at a rotational speed of 650 r/min for 2 h to obtain a novel crystal form F of trelagliptin.

Example 11

10 g of trelagliptin and 1 g of pepsase were accurately weighed and added to a 500 mL ball-milling tank (a mass ratio of the trelagliptin to the protein was 10:1), mill balls were added, the ball-milling tank was placed in a 25° C. ball mill, and ball-milling was conducted at a rotational speed of 500 r/min for 1 h to obtain a novel crystal form F of trelagliptin.

Example 12

20 g of trelagliptin and 0.2 g of ovalbumin were accurately weighed and added to a 500 mL ball-milling tank (a mass ratio of the trelagliptin to the protein was 100:1), mill balls were added, the ball-milling tank was placed in a 25° C. ball mill, and ball-milling was conducted at a rotational speed of 650 r/min for 3 h to obtain a novel crystal form F of trelagliptin.

Example 13

15 g of trelagliptin and 0.5 g of ovalbumin were accurately weighed and added to a 500 mL ball-milling tank (a mass ratio of the trelagliptin to the protein was 30:1), mill balls were added, the ball-milling tank was placed in a 35° C. ball mill, and ball-milling was conducted at a rotational speed of 650 r/min for 1 h to obtain a novel crystal form F of trelagliptin.

Example 14

15 g of trelagliptin and 0.5 g of ovalbumin were accurately weighed and added to a 500 mL ball-milling tank (a mass ratio of the trelagliptin to the protein was 30:1), mill balls were added, the ball-milling tank was placed in a 25° C. ball mill, and ball-milling was conducted at a rotational speed of 400 r/min for 3 h to obtain a novel crystal form F of trelagliptin.

Example 15

20 g of trelagliptin and 1 g of ovalbumin were accurately weighed and added to a 500 mL ball-milling tank (a mass ratio of the trelagliptin to the protein was 20:1), mill balls were added, the ball-milling tank was placed in a 15° C. ball mill, and ball-milling was conducted at a rotational speed of 650 r/min for 3 h to obtain a novel crystal form F of trelagliptin.

Example 16

10 g of trelagliptin and 1 g of ovalbumin were accurately weighed and added to a 500 mL ball-milling tank (a mass ratio of the trelagliptin to the protein was 10:1), mill balls were added, the ball-milling tank was placed in a 25° C. ball mill, and ball-milling was conducted at a rotational speed of 650 r/min for 1.5 h to obtain a novel crystal form F of trelagliptin.

In order to prove an effect of the novel crystal form F of trelagliptin provided in the present disclosure, solubilities of the original crystal form I of trelagliptin and the novel crystal form F of trelagliptin in deionized water, a sodium phosphate buffer solution with a pH of 6.8, a buffer solution with a pH of 7.4, and a buffer solution with a pH of 1.2 were tested, and specific operations were as follows: 100 mg of each of the crystal forms I and F of trelagliptin was weighed and added to 50 mL of deionized water, and a resulting mixture was stirred at a water temperature of 37° C. and a rotational speed of 20 rpm for 24 h to allow a solubility equilibrium; then a sample was taken and filtered through a 0.45 μm filter membrane, and an appropriate amount of a resulting filtrate was taken and tested for absorbance at 279 nm according to ultraviolet-visible (UV-vis) spectrophotometry; and resulting absorbance values each were substituted into a standard curve to obtain solubilities of the different crystal forms of trelagliptin, as shown in Table 1.

TABLE 1

Solubility of trelagliptin in different dissolutions

| Dissolution | Solubility (mg/mL) | |
| --- | --- | --- |
| medium | Crystal form I | Crystal form F |
| Deionized water | 3.40 | 8.51 |
| pH = 6.8 | 15.46 | 32.78 |
| pH = 7.4 | 12.94 | 30.54 |
| pH = 1.2 | 42.67 | 73.61 |

The results in Table 1 show that the novel crystal form F of trelagliptin has significantly-higher solubilities than the original crystal form I of trelagliptin in the deionized water, sodium phosphate buffer solution with a pH of 6.8, buffer solution with a pH of 7.4, and buffer solution with a pH of 1.2.

Stability

According to the Guidelines for Stability Tests of Active Pharmaceutical Ingredients (APIs) and Formulations, the stability of the novel crystal form F of trelagliptin was tested.

High-temperature test: The novel crystal form F of trelagliptin was spread in a petri dish and then placed in a drying oven at 60° C. for 10 d, where on day 5 and day 10, a sample was taken and subjected to XRPD analysis to determine whether the crystal form was stable.

High-humidity test: The novel crystal form F of trelagliptin was spread in petri dishes, and then the petri dishes were placed in constant-temperature and constant-humidity incubators respectively with relative humidities of 90% and 75% at 25° C. for 10 d, where on day 5 and day 10, a sample was taken and subjected to XRPD analysis to determine whether the crystal form was stable.

Strong light irradiation test: The novel crystal form F of trelagliptin was spread in a petri dish and then placed in a strong light irradiation test chamber with illuminance of 4500 lx±500 lx for 10 d, where on day 5 and day 10, a sample was taken and subjected to XRPD analysis to determine whether the crystal form was stable.

Experimental results show that the high temperature, the high humidity, and the strong light irradiation have no impact on the stability of the novel crystal form F of trelagliptin.

Moisture Absorption

The dried novel crystal form F of trelagliptin prepared in this example was spread in a weighing bottle, then placed in a constant-temperature and constant-humidity incubator with a humidity of 80% RH and a temperature of 25° C. for 24 h, and then weighed. Experimental results show that a weight gain of the novel crystal form F of trelagliptin is less than 0.4%.

What is claimed is:

1. A method for preparing a crystal form F of trelagliptin, comprising: adding a trelagliptin and a mediating protein to an agate ball-milling tank, adding agate mill balls, and conducting mechanical ball-milling at 10° C. to 40° C. for 0.5 h to 6 h to obtain the crystal form F of trelagliptin;

wherein an X-ray powder diffraction (XRPD) pattern of the crystal form F of trelagliptin has corresponding characteristic diffraction peaks at 2θ values of 11.47°, 12.41°, 13.21°, 14.46°, 16.13°, 16.93°, 17.40°, 18.49°, 19.24°, 19.80°, 20.37°, 21.76°, 22.76°, 23.21°, 23.75°, 25.08°, 25.52°, 26.02°, 28.02°, 29.54°, 30.92°, 34.12°, and 34.98°; and a mass ratio of the trelagliptin to the mediating protein is (2-120):1.

2. The method according to claim 1, wherein the mechanical ball-milling is conducted at a rotational speed of 400 r/min to 650 r/min.

* * * * *